(12) United States Patent
Nishiyama et al.

(10) Patent No.: US 8,295,718 B2
(45) Date of Patent: Oct. 23, 2012

(54) CONCENTRATION DETECTION APPARATUS AND IMAGE FORMATION APPARATUS

(75) Inventors: Kazuhiro Nishiyama, Shiojiri (JP); Akihiro Gomi, Fujimi-machi (JP); Tsutomu Sasaki, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 533 days.

(21) Appl. No.: 12/566,407

(22) Filed: Sep. 24, 2009

(65) Prior Publication Data
US 2010/0086297 A1    Apr. 8, 2010

(30) Foreign Application Priority Data

Oct. 8, 2008 (JP) ................................. 2008-261832

(51) Int. Cl.
*G03G 15/08* (2006.01)
(52) U.S. Cl. .......................................................... 399/30
(58) Field of Classification Search .................. 399/30, 399/57, 58, 61, 62, 64, 120, 358, 359
See application file for complete search history.

(56) References Cited

U.S. PATENT DOCUMENTS

| | | | | |
|---|---|---|---|---|
| 6,515,747 B1 | 2/2003 | Satoh et al. | ................... | 356/436 |
| 7,778,576 B2 * | 8/2010 | Tanjo et al. | ................... | 399/238 |
| 7,885,565 B2 * | 2/2011 | Sasaki et al. | ................... | 399/57 |
| 8,005,382 B2 * | 8/2011 | Tanaka | ................... | 399/57 |
| 8,005,383 B2 * | 8/2011 | Tanaka et al. | ................... | 399/57 |
| 8,005,384 B2 * | 8/2011 | Tanaka | ................... | 399/57 |
| 8,014,691 B2 * | 9/2011 | Inukai et al. | ................... | 399/57 |
| 8,023,848 B2 * | 9/2011 | Inukai et al. | ................... | 399/64 |
| 8,036,555 B2 * | 10/2011 | Tanaka et al. | ................... | 399/57 |

FOREIGN PATENT DOCUMENTS

JP    2000-249653    9/2000

OTHER PUBLICATIONS

Machine translation of reference Ueda et al. (JP 2007-271,777 A) Publication date Oct. 18, 2007.*

* cited by examiner

*Primary Examiner* — Walter L Lindsay, Jr.
*Assistant Examiner* — Rodney Bonnette
(74) *Attorney, Agent, or Firm* — DLA Piper LLP (US)

(57) ABSTRACT

A concentration detection apparatus includes: a light-emitting element that emits light; a light-emitting-element holding unit that holds the light-emitting element; a light-receiving element that receives light emitted from the light-emitting element; a light-receiving-element holding unit that holds the light-receiving element and is provided opposite to the light-emitting-element holding unit with a gap therebetween; a moving unit that can move through or at the gap between the light-emitting-element holding unit and the light-receiving-element holding unit; and a gap adjusting unit that adjusts a value of the gap as a distance between the light-emitting-element holding unit and the light-receiving-element holding unit.

5 Claims, 12 Drawing Sheets

CONCENTRATION DETECTION APPARATUS AND IMAGE FORMATION APPARATUS

BACKGROUND

1. Technical Field

The present invention relates a concentration detection apparatus that detects the concentration of liquid toner that includes carrier liquid and toner. The invention further relates to an image formation apparatus.

2. Related Art

An example of methods for detecting the concentration of liquid with the use of a liquid carrying roller is disclosed in JP-A-2000-249653. The liquid carrying roller disclosed therein is made up of an eccentric disk unit and two sandwiching disk units. The diameter of one of the two sandwiching disk units is the same as that of the other. In addition, the diameter of each sandwiching disk unit is larger than that of the eccentric disk unit. The eccentric disk unit is sandwiched between the two sandwiching disk units. Liquid whose concentration is to be detected is filled into a circumferential recess formed in a step between the eccentric disk unit and the two sandwiching disk units to have a plurality of thicknesses different from each other according to the step. Then, on the basis of the output of an optical sensor for the plurality of thicknesses, the concentration of the liquid is detected.

However, the technique disclosed in JP-A-2000-249653 has a problem in that output sensitivity fluctuates depending on the transmittance of liquid whose concentration is to be measured.

SUMMARY

An advantage of some aspects of the invention to provide a liquid concentration apparatus and an image formation apparatus that can measure liquid concentration accurately even when the transmission factor of detection target liquid, that is, liquid whose concentration is to be measured, varies.

In order to address the above-identified problem without any limitation thereto, a concentration detection apparatus according to a first aspect of the invention includes: a light-emitting element that emits light; a light-emitting-element holding section that holds the light-emitting element; a light-receiving element that receives light emitted from the light-emitting element; a light-receiving-element holding section that holds the light-receiving element and is provided opposite to the light-emitting-element holding section with a gap therebetween; a moving section that can move through or at the gap between the light-emitting-element holding section and the light-receiving-element holding section; and a gap adjusting section that adjusts a value of the gap as a distance between the light-emitting-element holding section and the light-receiving-element holding section.

In the configuration of a concentration detection apparatus according to the first aspect of the invention, it is preferable that the gap adjusting section should include a spacer that is provided between the light-emitting-element holding section and the light-receiving-element holding section and should further include a joining section that joins the light-emitting-element holding section and the light-receiving-element holding section with the spacer being provided therebetween.

In the preferred configuration of a concentration detection apparatus described above, the spacer may be an elastic member.

In the configuration of a concentration detection apparatus according to the first aspect of the invention, the moving section may have flexibility.

An image formation apparatus according to a second aspect of the invention includes: a first container that contains a first liquid developer; a first image carrier; a first developing section that develops a latent image formed on the first image carrier by means of the first liquid developer; a first concentration detecting section that is provided in the first container, the first concentration detecting section including a first light-emitting element that emits light, a first light-emitting-element holding section that holds the first light-emitting element, a first light-receiving element that receives light emitted from the first light-emitting element, a first light-receiving-element holding section that holds the first light-receiving element and is provided opposite to the first light-emitting-element holding section with a first gap therebetween, and a first moving section that can move through or at the first gap; a second container that contains a second liquid developer; a second image carrier; a second developing section that develops a latent image formed on the second image carrier by means of the second liquid developer; a second concentration detecting section that is provided in the second container, the second concentration detecting section including a second light-emitting element that emits light, a second light-emitting-element holding section that holds the second light-emitting element, a second light-receiving element that receives light emitted from the second light-emitting element, a second light-receiving-element holding section that holds the second light-receiving element and is provided opposite to the second light-emitting-element holding section with a second gap therebetween, and a second moving section that can move through or at the second gap; and a transfer member onto which an image formed on the first image carrier and an image formed on the second image carrier are transferred.

In the configuration of an image formation apparatus according to the second aspect of the invention, it is preferable that the first concentration detecting section should further include a first gap adjusting section that adjusts the first gap; and the second concentration detecting section should further include a second gap adjusting section that adjusts the second gap.

The image formation apparatus according to the second aspect of the invention should further include: a third container that contains a third liquid developer; a third image carrier; a third developing section that develops a latent image formed on the third image carrier by means of the third liquid developer; a third concentration detecting section that is provided in the third container, the third concentration detecting section including a third light-emitting element that emits light, a third light-emitting-element holding section that holds the third light-emitting element, a third light-receiving element that receives light emitted from the third light-emitting element, a third light-receiving-element holding section that holds the third light-receiving element and is provided opposite to the third light-emitting-element holding section with a third gap therebetween, and a third moving section that can move through or at the third gap; a fourth container that contains a fourth liquid developer; a fourth image carrier; a fourth developing section that develops a latent image formed on the fourth image carrier by means of the fourth liquid developer; and a fourth concentration detecting section that is provided in the fourth container, the fourth concentration detecting section including a fourth light-emitting element that emits light, a fourth light-emitting-element holding section that holds the fourth light-emitting element, a fourth light-receiving element that receives light emitted from the fourth light-emitting element, a fourth light-receiving-element holding section that holds the fourth light-receiving element and is provided opposite to the fourth light-emitting-element holding section with a fourth gap therebetween, and a fourth moving section that can move through or at the fourth gap.

With the structure of a concentration detection apparatus according to the first aspect of the invention, it is possible to adjust a gap between a light-emitting element and a light-receiving element depending on the transmission factor of liquid whose concentration is to be measured, thereby improving precision in concentration detection.

In addition, a concentration detection apparatus according to the first aspect of the invention offers cost reduction with a simple structure.

Moreover, a concentration detection apparatus according to the first aspect of the invention prevents or reduces the stagnation of liquid in the gap between the light-emitting element and the light-receiving element, thereby improving precision in concentration detection.

With the structure of an image formation apparatus according to the second aspect of the invention, it is possible to adjust a gap between a light-emitting element and a light-receiving element depending on the colors of liquid developers having transmission factors different from one another. Therefore, it is possible to improve precision in concentration detection and thus form an image in high quality.

BRIEF DESCRIPTION OF THE DRAWINGS

The invention will be described with reference to the accompanying drawings, wherein like numbers reference like elements.

DESCRIPTION OF EXEMPLARY EMBODIMENTS

With reference to the accompanying drawings, exemplary embodiments of the present invention will now be explained in detail.

Figure 1:
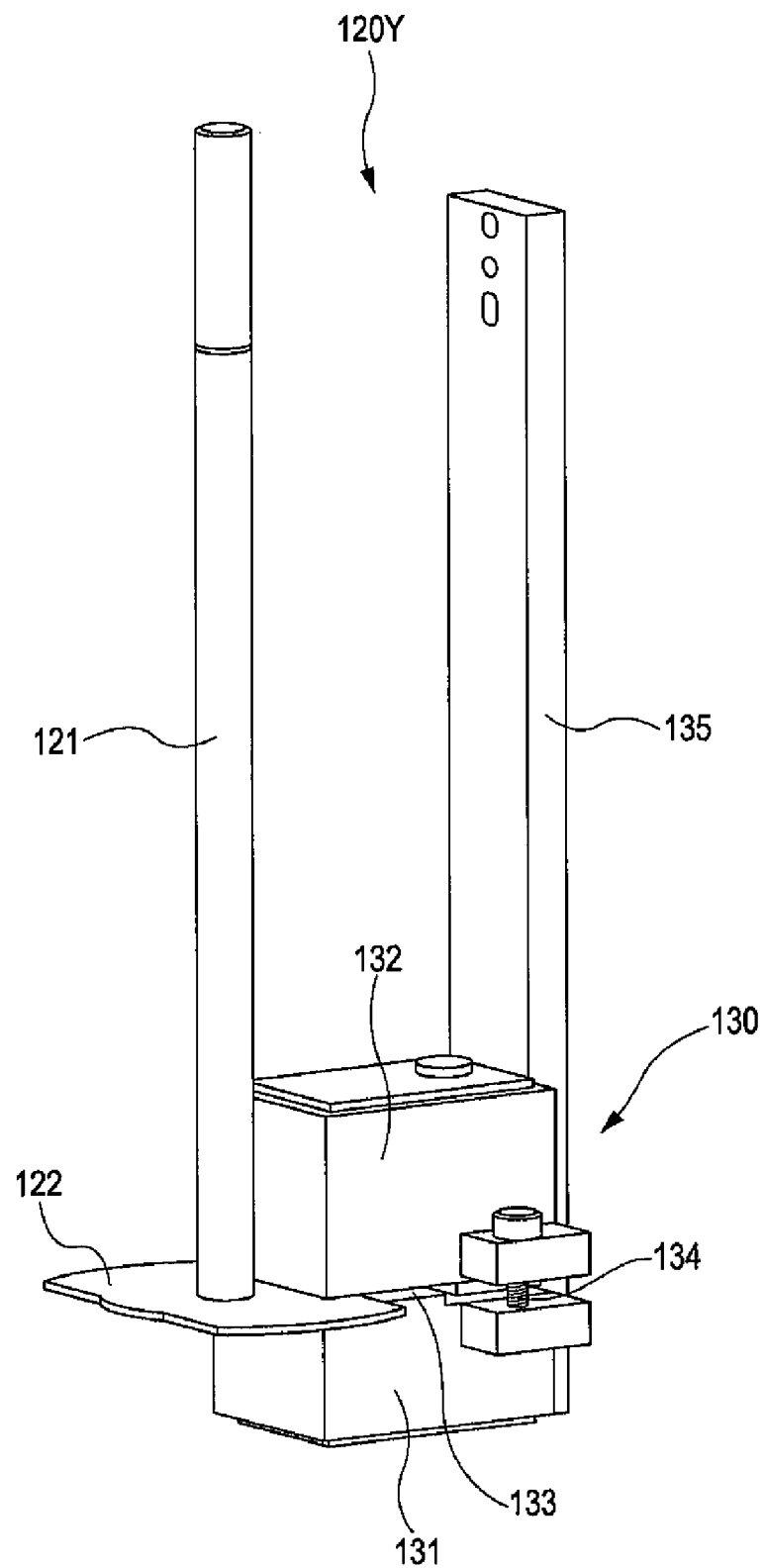
FIG. 1 is a perspective view that schematically illustrates an example of the configuration of a concentration detection apparatus according to a first embodiment of the invention.

FIG. 1 is a perspective view that schematically illustrates an example of the configuration of a concentration detection apparatus according to a first embodiment of the invention. As illustrated in FIG. 1, a concentration detection apparatus 120 is provided with a rotating shaft 121, a transparent propeller 122, a concentration detection unit 130, and a detection-unit mounting member 135. The transparent propeller 122 is an example of a moving section according to an aspect of the invention.

The transparent propeller 122, which has flexibility, is mounted on the rotating shaft 121. A driving motor or the like that is not illustrated in the drawing supplies power to the rotating shaft 121. The transparent propeller 122 turns together with the rotating shaft 121 when driven by the motor. The concentration detection unit 130 is mounted on the detection-unit mounting member 135. The concentration detection unit 130 includes a light-emitting member 131, a light-receiving member 132, and a screw 134. A clearance 133 is formed between the light-emitting member 131 and the light-receiving member 132. The screw 134 is used for joining the light-emitting member 131 with the light-receiving member 132. The clearance 133 is an example of a gap according to an aspect of the invention. The screw 134 is an example of a joining section according to an aspect of the invention.

Figure 2:
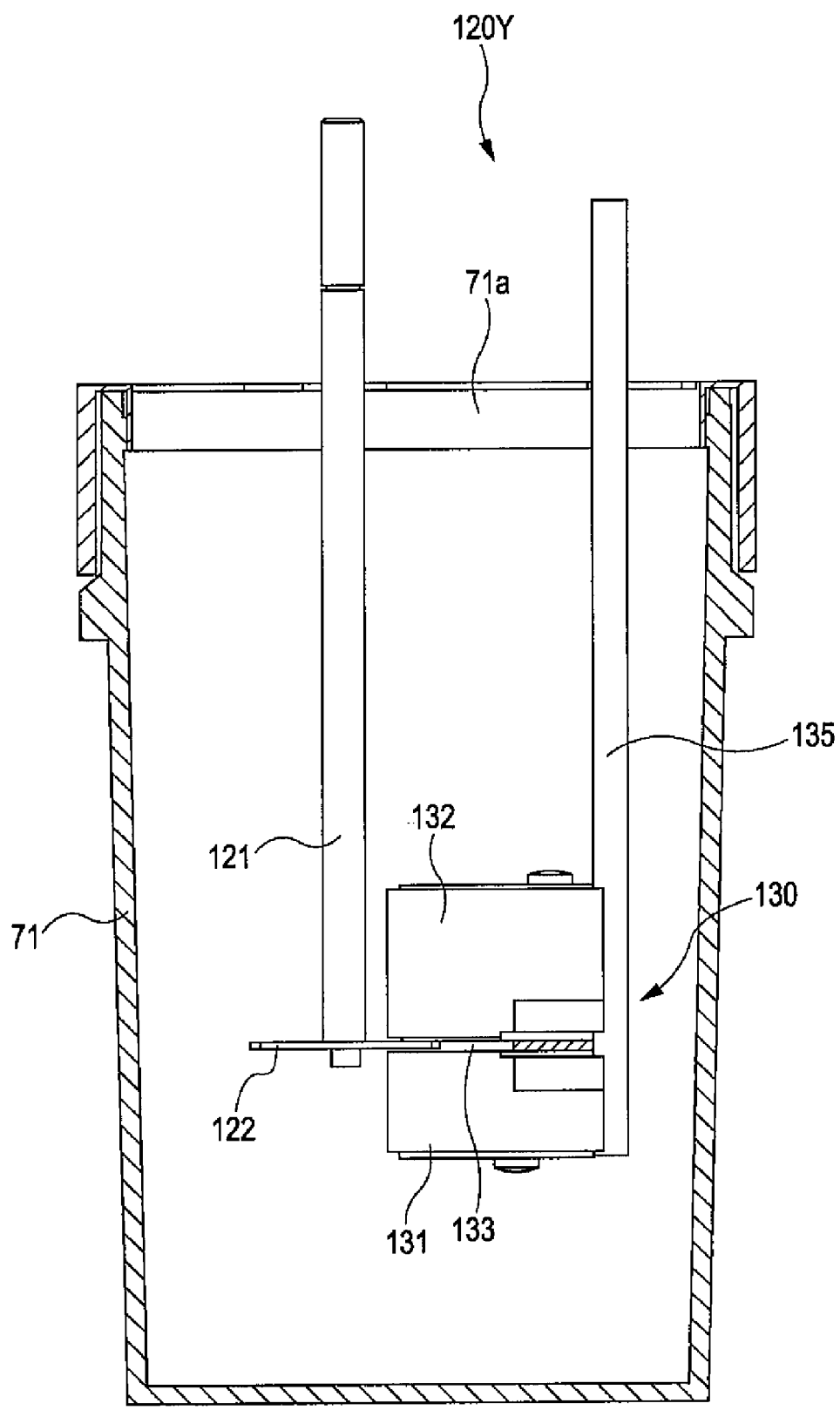
FIG. 2 is a front view that schematically illustrates an example of the configuration of a concentration detection apparatus that is encased in a liquid-containing member according to an exemplary embodiment of the invention.

FIG. 2 is a front view that schematically illustrates an example of the configuration of a concentration detection apparatus that is encased in a liquid-containing member according to an exemplary embodiment of the invention. As illustrated in FIG. 2, a containing member 71, which serves as a liquid container, is provided with a concentration detection apparatus support member 71a. The containing member 71 supports the rotating shaft 121 of the concentration detection apparatus 120 in a rotatable manner. In addition, the containing member 71 supports the detection-unit mounting member 135.

Figure 3:
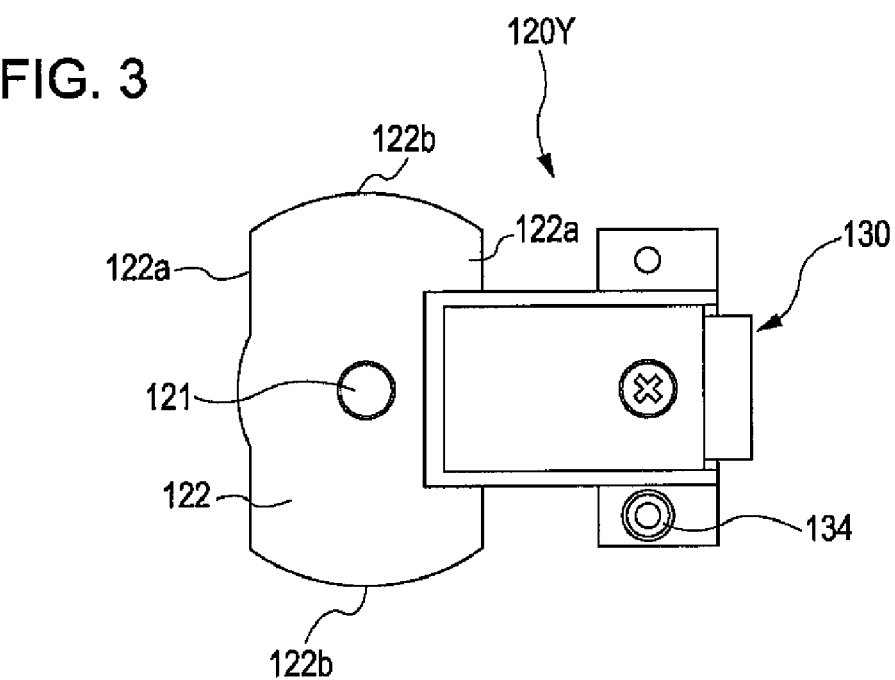
FIG. 3 is a top view that schematically illustrates an example of a concentration detection unit and some neighboring components according to an exemplary embodiment of the invention.

FIG. 3 is a top view that schematically illustrates an example of a concentration detection unit and some neighboring components according to an exemplary embodiment of the invention. As illustrated in FIG. 3, the transparent propeller 122 is a plate member that has first edges 122a and second edges 122b. The second edge 122b is shorter than the first edge 122a.

Figure 4:
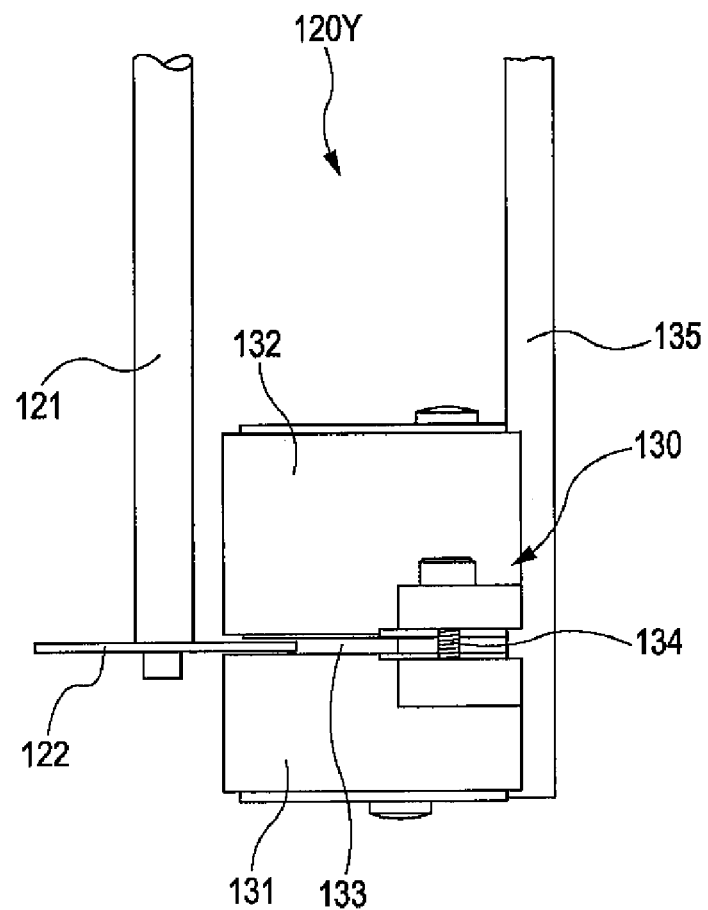
FIG. 4 is a front view that schematically illustrates an example of a concentration detection unit and some neighboring components according to an exemplary embodiment of the invention.

FIG. 4 is a front view that schematically illustrates an example of a concentration detection unit and some neighboring components according to an exemplary embodiment of the invention. A blade part of the transparent propeller 122 passes through the clearance 133 when the rotating shaft 121 rotates. A flange of the light-emitting member 131 and a flange of the light-receiving member 132 are fastened to each other with the screw 134.

Figure 5:
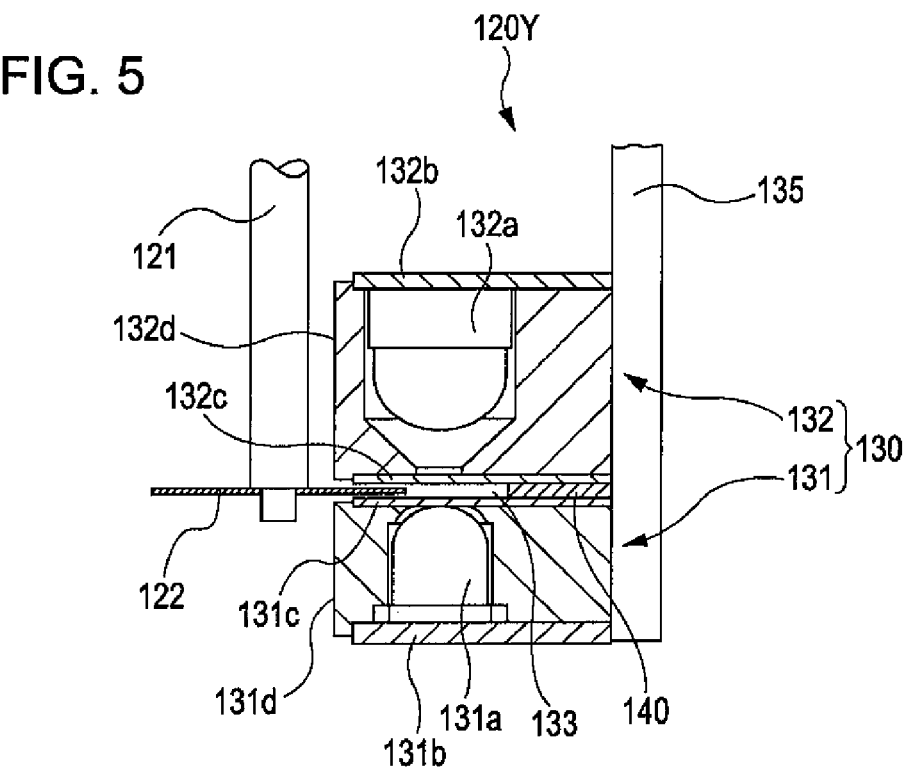
FIG. 5 is a sectional view that schematically illustrates an example of a concentration detection unit and some neighboring components according to an exemplary embodiment of the invention.

FIG. 5 is a sectional view that schematically illustrates an example of a concentration detection unit and some neighboring components according to an exemplary embodiment of the invention.

The light-emitting member 131 includes a light-emitting element 131a, a light-emitting-element mounting plate 131b, a first transmitting member 131c, and a light-emitting-element holder 131d. An example of the light-emitting element 131a is a light emitting diode (LED). The light-emitting element 131a is mounted on the light-emitting-element mounting plate 131b. The first transmitting member 131c faces the clearance 133. An example of the first transmitting member 131c is a glass plate. The light-emitting-element holder 131d is a member that holds the light-emitting element 131a, the light-emitting-element mounting plate 131b, and the first transmitting member 131c. The light-emitting-element mounting plate 131b, the first transmitting member 131c, and/or the light-emitting-element holder 131d constitute an example of a light-emitting-element holding section according to an aspect of the invention.

The light-receiving member 132 includes a light-receiving element 132a, a light-receiving-element mounting plate 132b, a second transmitting member 132c, and a light-receiving-element holder 132d. The light-receiving element 132a is mounted on the light-receiving-element mounting plate 132b. The second transmitting member 132c faces the clearance 133. An example of the second transmitting member 132c is a glass plate. The light-receiving-element holder 132d is a member that holds the light-receiving element 132a, the light-receiving-element mounting plate 132b, and the second transmitting member 132c. The light-receiving-element mounting plate 132b, the second transmitting member 132c, and/or the light-receiving-element holder 132d constitute an example of a light-receiving-element holding section according to an aspect of the invention.

A spacer 140 is provided adjacent to the detection-unit mounting member 135 between the light-emitting member 131 and the light-receiving member 132. The clearance 133 is formed therebetween at the opposite side, which is closer to the transparent propeller 122. The spacer 140 is an example of a gap adjusting section according to an aspect of the invention. The spacer 140 may be an elastic member.

Figure 6:
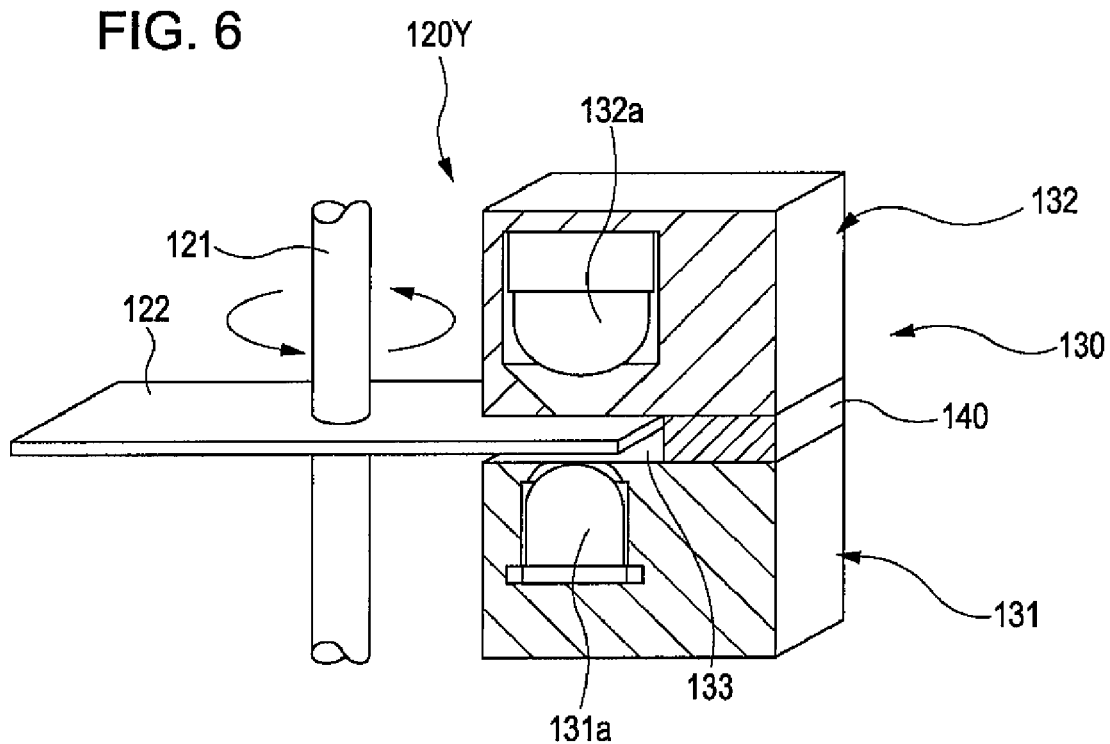
FIG. 6 is an enlarged view that schematically illustrates an example of a concentration detection unit during concentration detection shown together with some neighboring components according to an exemplary embodiment of the invention.

Next, the operation of the concentration detection apparatus 120 is explained below. FIG. 6 is an enlarged view that schematically illustrates an example of a concentration detection unit during concentration detection shown together with some neighboring components according to an exemplary embodiment of the invention.

As illustrated in FIG. 6, the transparent propeller 122 is a flat member that has the shape of a rectangle or the like. The transparent propeller 122 is supported rotatably on the rotating shaft 121. The transparent propeller 122 is provided at a given height/position where a blade part thereof can enter the clearance 133 between the light-emitting element 131a, which is provided in the light-emitting member 131 of the concentration detection unit 130, and the light-receiving element 132a, which is provided in the light-receiving member 132 thereof.

During the detection of concentration (i.e., density), a part of the transparent propeller 122 is positioned on a propagation path of light that is emitted from the light-emitting element 131a and enters the light-receiving element 132a. When the transparent propeller 122 is provided on the optical path from the light-emitting element 131a to the light-receiving element 132a, the "thickness" of liquid that is present on the optical path is reduced, resulting in increased transmittance. With the increased transmission factor, it is possible to detect the concentration of liquid with high precision.

Figure 7:
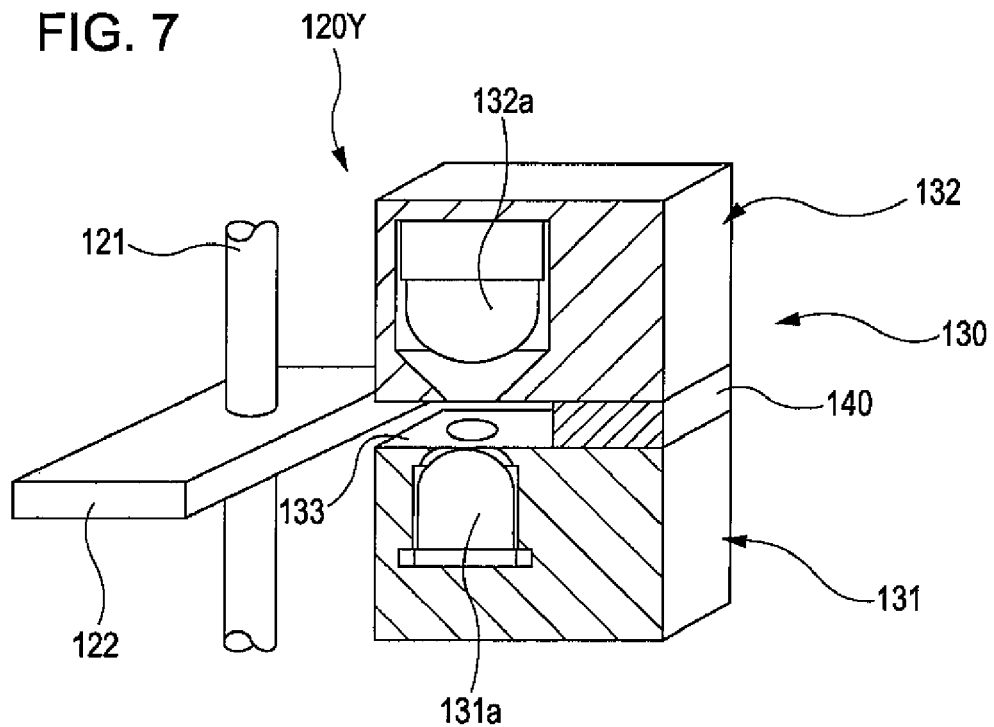
FIG. 7 is a diagram that schematically illustrates an example of a state in which a transparent propeller has turned from the state illustrated in FIG. 6 to change its blade orientation.

FIG. 7 is a diagram that schematically illustrates an example of a state in which the transparent propeller has turned from the state illustrated in FIG. 6 to change its blade orientation. As illustrated in FIG. 7, the transparent propeller 122 can rotate around the rotating shaft 121. Through the rotation of the transparent propeller 122 around the rotating shaft 121, liquid that is present in the clearance 133 is swept out, which causes new liquid to flow into the clearance 133. Accordingly, liquid does not stagnate in the clearance 133, which results in improved precision in concentration detection.

Figure 8:
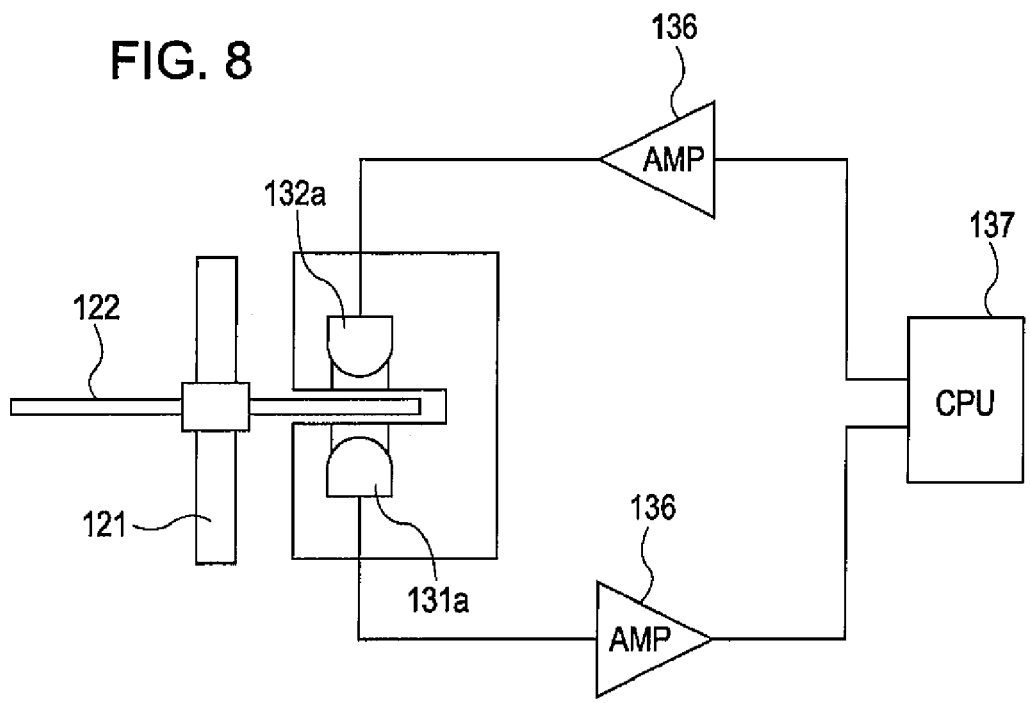
FIG. 8 is a diagram that schematically illustrates an example of the system configuration of a concentration detection unit according to an exemplary embodiment of the invention.

FIG. 8 is a diagram that schematically illustrates an example of the system configuration of a concentration detection unit according to an exemplary embodiment of the invention. The light-emitting element 131a and the light-receiving element 132a are connected to a CPU 137 via amplifiers 136, respectively. The CPU 137 is an example of a controlling section according to an aspect of the invention.

Figure 9:
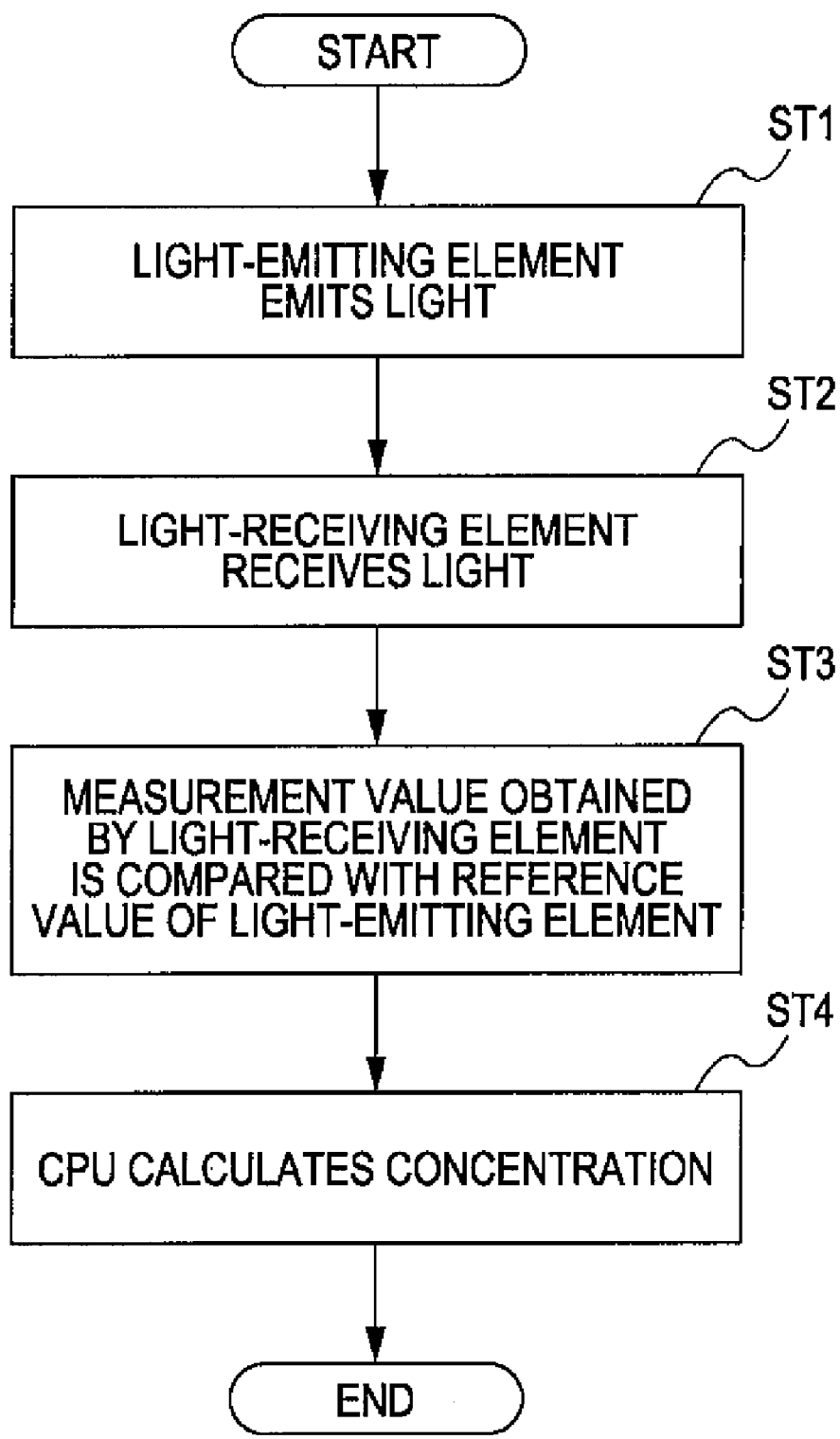
FIG. 9 is a flowchart that schematically illustrates an example of the detecting operation of a concentration detection apparatus according to an exemplary embodiment of the invention.

Next, a method of detecting concentration performed by the concentration detection apparatus 120 is explained below. FIG. 9 is a flowchart that schematically illustrates an example of the detecting operation of a concentration detection apparatus according to an exemplary embodiment of the invention.

In a first step, the light-emitting element 131a is turned ON to emit light (ST1). Next, in a second step, the light-receiving element 132a receives light emitted from the light-emitting element 131a (ST2).

Then, in a third step, a measurement value obtained by the light-receiving element 132a is compared with a predetermined reference value of the light-emitting element 131a (ST3). Subsequently, in a fourth step, the CPU 137 calculates the concentration of liquid in accordance with an arithmetic expression, a map, or the like (ST4).

With the concentration detection method explained above, it is possible to detect the concentration of liquid contained in the containing member 71.

Figure 10:
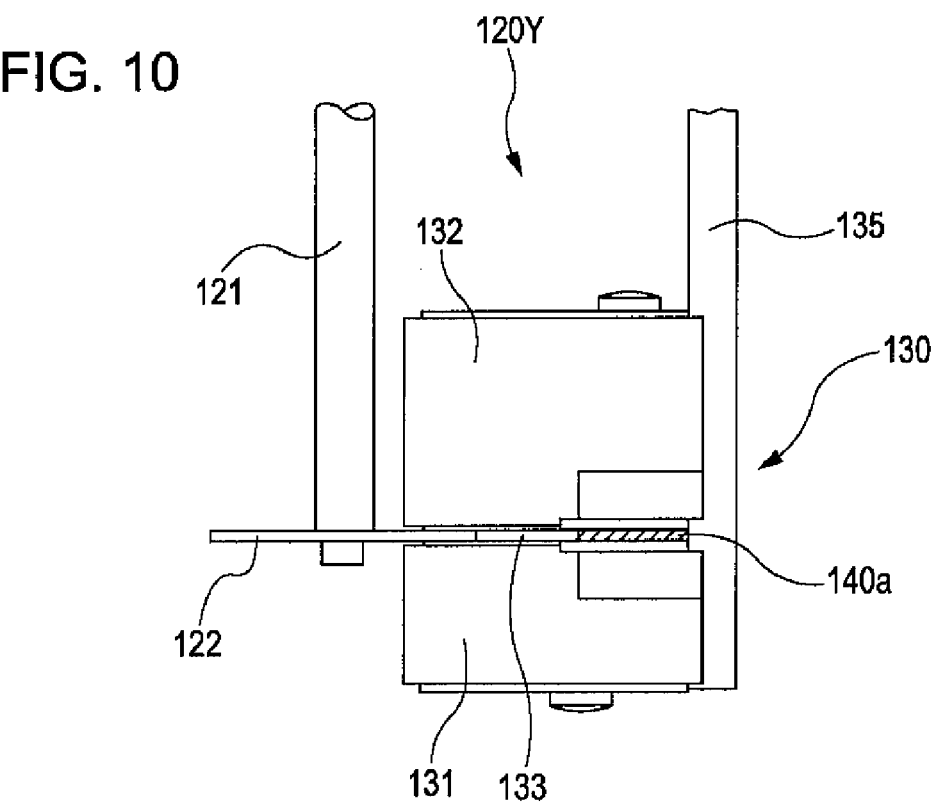
FIG. 10 is an enlarged view that schematically illustrates an example of a concentration detection unit and some neighboring components according to the first embodiment of the invention.
Figure 11:
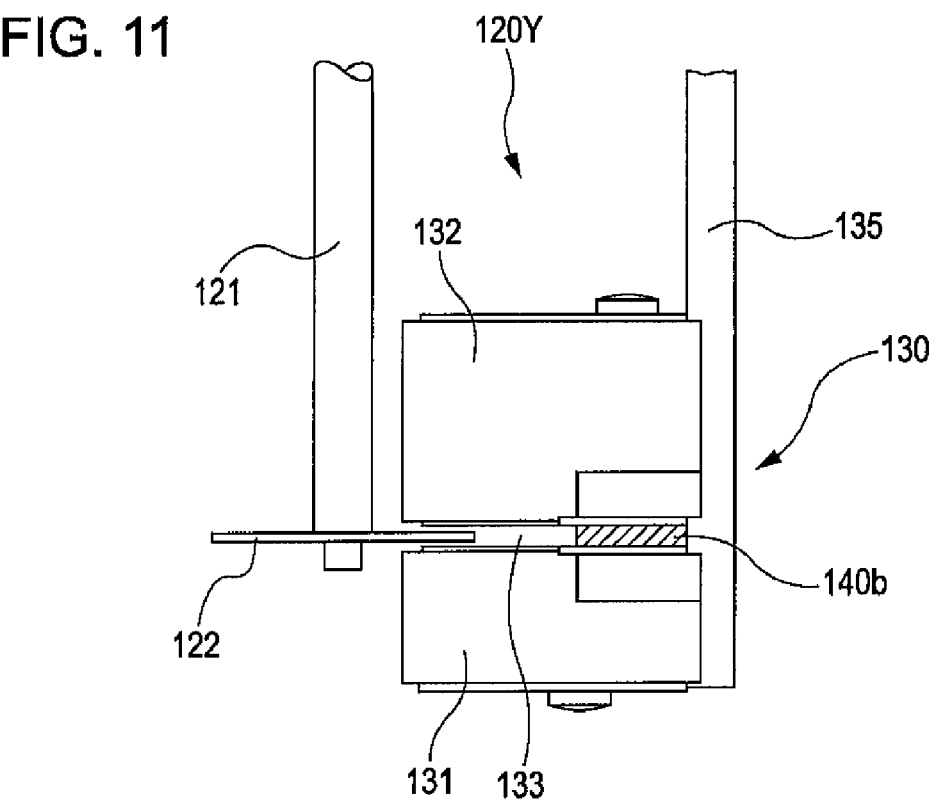
FIG. 11 is an enlarged view that schematically illustrates another example of a concentration detection unit and some neighboring components according to the first embodiment of the invention.

Each of FIGS. 10 and 11 is an enlarged view that schematically illustrates an example of a concentration detection unit and some neighboring components according to a first embodiment of the invention. The spacer 140 provided in the concentration detection unit 130 according to the first embodiment of the invention is a replaceable component. Specifically, the spacer 140 is replaceable depending on the transmission factor of detection target liquid, that is, liquid whose concentration is to be detected. Accordingly, the thickness of liquid that is present on an optical path can be adjusted through the replacement of the spacers 140. By this means, it is possible to detect the concentration of the liquid with high precision.

For example, a spacer 140a illustrated in FIG. 10 is thinner than a spacer 140b illustrated in FIG. 11. Even in a case where the transmission factor of detection target liquid is low, the thickness of liquid that is present on an optical path can be reduced with the use of the spacer 140a illustrated in FIG. 10. Thus, it is possible to detect the concentration of the liquid with high precision.

Figure 12:
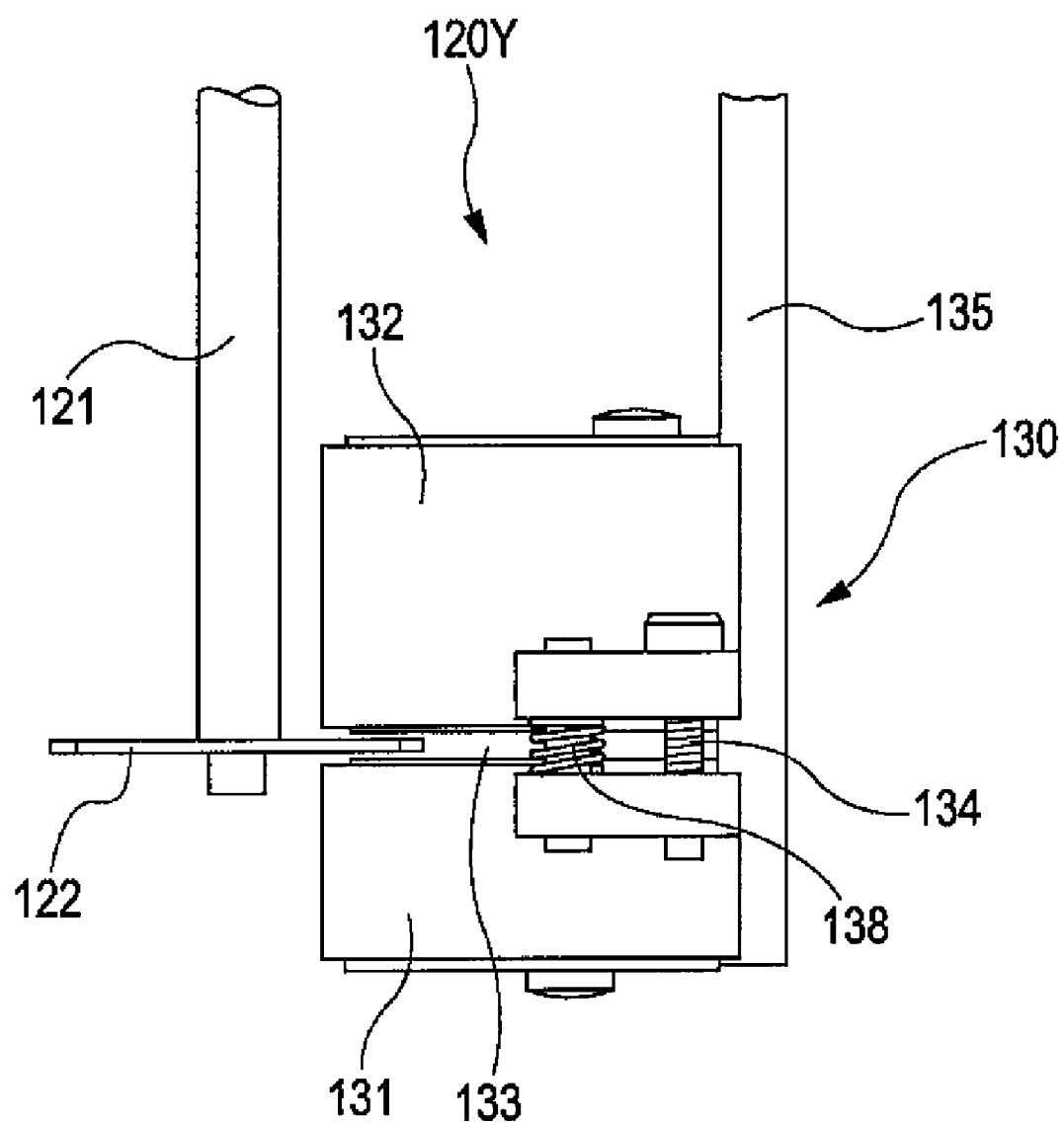
FIG. 12 is an enlarged view that schematically illustrates an example of a concentration detection unit and some neighboring components according to a second embodiment of the invention.

FIG. 12 is an enlarged view that schematically illustrates an example of a concentration detection unit and some neighboring components according to a second embodiment of the invention. In the structure of a concentration detection unit according to the second embodiment of the invention, a spring 138 is provided as an elastic member between the light-emitting member 131 and the light-receiving member 132. In addition, the screw 134 is provided as a joining section that joins the light-emitting member 131 with the light-receiving member 132. The clearance between the light-emitting member 131 and the light-receiving member 132 can be adjusted thereby. The spring 138 and the screw 134 constitute a gap adjusting section according to an aspect of the invention.

With such a structure, the thickness of liquid that is present on an optical path can be adjusted progressively through the rotation of the screw 134 depending on the transmission factor of detection target liquid. Therefore, it is possible to detect the concentration of the liquid with greater precision. For example, even in a case where the transmission factor of detection target liquid is low, the thickness of liquid that is present on an optical path can be reduced through the rotation of the screw 134, which makes it possible to detect the concentration of the liquid with high precision.

Next, an example of the application of the concentration detection apparatus 120 to an image formation apparatus is explained below.

Figure 13:
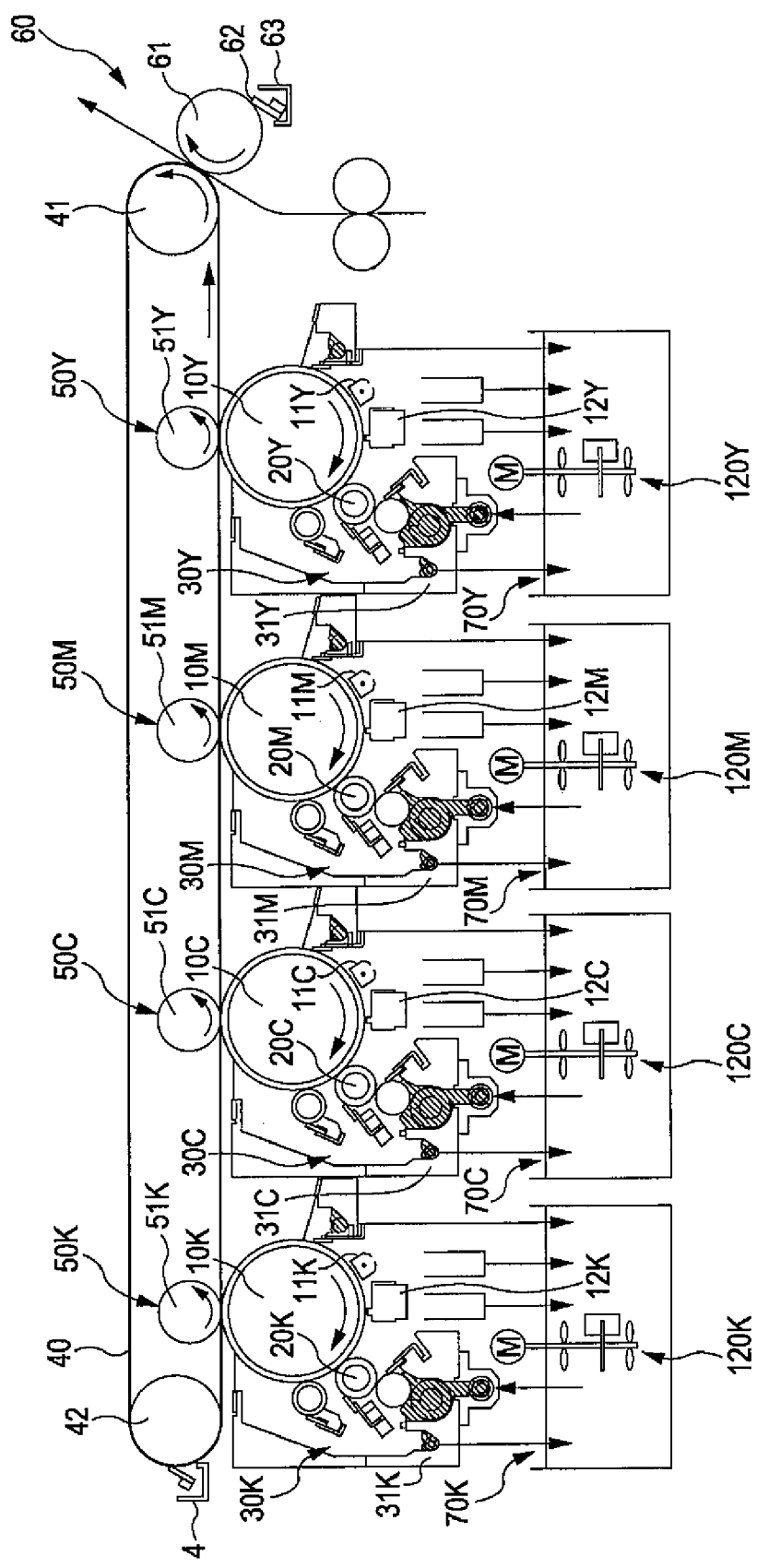
FIG. 13 is a diagram that schematically illustrates an example of main components of an image formation apparatus according to an exemplary embodiment of the invention.

FIG. 13 is a diagram that schematically illustrates an example of main components of an image formation apparatus according to an exemplary embodiment of the invention. In the present embodiment of the invention, a liquid developer for four colors of black K, cyan C, yellow Y, and magenta M is used. Black is an example of a first color according to an aspect of the invention. Cyan, yellow, and magenta correspond to second, third, and fourth colors according to an aspect of the invention, respectively. A member that uses the black developer is an example of a first member according to an aspect of the invention. Members that use the cyan developer, the yellow developer, and the magenta developer respectively correspond to second, third, and fourth members according to an aspect of the invention.

An image formation unit is provided with image carriers 10Y, 10M, 10C, and 10K, corona electrical charging devices 11Y, 11M, 11C, and 11K, and light exposure units 12Y, 12M, 12C, and 12K. The light exposure unit 12Y, 12M, 12C, 12K includes a line head that is made up of an array of LEDs. The corona electrical charging devices 11Y, 11M, 11C, and 11K electrify the image carriers 10Y, 10M, 10C, and 10K uniformly. Then, on the basis of an inputted image signal, the light exposure units 12Y, 12M, 12C, and 12K perform lighting control to form an electrostatic latent image on the electrified image carriers 10Y, 10M, 10C, and 10K, respectively.

Developing units 30Y, 30M, 30C, and 30K include developing rollers 20Y, 20M, 20C, and 20K, developer containers 31Y, 31M, 31C, and 31K, developer supply rollers 32Y, 32M, 32C, and 32K, and the like, respectively. The developer containers 31Y, 31M, 31C, and 31K contain the liquid developers of yellow Y, magenta M, cyan C, and black K, respectively. The developer supply rollers 32Y, 32M, 32C, and 32K are used for supplying the liquid developers of the respective colors from the respective developer containers 31Y, 31M, 31C, and 31K to the respective developing rollers 20Y, 20M, 20C, and 20K. Having these components, the developing units 30Y, 30M, 30C, and 30K develop the electrostatic latent image formed on the image carriers 10Y, 10M, 10C, and 10K with the use of the liquid developers of the respective colors.

An intermediary image transfer member 40 is an endless belt. The intermediary image transfer member 40 is stretched between a driving roller 41 and a tension roller 42. The intermediary image transfer member 40 turns under a turning force applied by the driving roller 41 while being in contact with the image carriers 10Y, 10M, 10C, and 10K at positions where primary image transfer units 50Y, 50M, 50C, and 50K are also in contact therewith, respectively. The primary image transfer units 50Y, 50M, 50C, and 50K respectively include primary image transfer rollers 51Y, 51M, 51C, and 51K. The primary image transfer rollers 51Y, 51M, 51C, and 51K are provided opposite to the image carriers 10Y, 10M, 10C, and 10K, respectively, with the intermediary image transfer member 40 being pinched therebetween. The primary image transfer units 50Y, 50M, 50C, and 50K sequentially transfer the developed toner images of the respective colors, which are formed on the image carriers 10Y, 10M, 10C, and 10K, onto the intermediary image transfer member 40 one on another, thereby forming a full color toner image thereon. Image transfer is performed at the positions of contact of the primary image transfer rollers 51Y, 51M, 51C, and 51K and the image carriers 10Y, 10M, 10C, and 10K (i.e., image transfer positions).

A secondary image transfer unit 60 includes a secondary image transfer roller 61 and a cleaning device, which is made up of a secondary image transfer roller cleaning blade 62 and a developer recovery unit 63. The secondary image transfer roller 61 is provided opposite to the driving roller 41 with the intermediary image transfer member 40 being pinched therebetween. In synchronization with the arrival of a full color toner image, which has been transferred on the intermediary image transfer member 40 as a result of color overlay, or a single color toner image transferred thereon to a transfer position of the secondary image transfer unit 60, a sheet material such as paper, film, cloth, or the like is transported on a sheet transportation path L. The secondary image transfer unit 60 transfers the full color toner image or the single color toner image onto the sheet material fed to the transfer position as a secondary transfer process.

An image fixation unit, which is not illustrated in the drawing, is provided at a downstream position on the sheet transportation path L. The image fixation unit applies heat and pressure to the recording target medium such as printing paper to fix the full color toner image or the single color toner image thereon. In this way, a final image is formed on the sheet.

A cleaning device that includes an intermediary image transfer member cleaning blade 46 and a developer recovery unit 47 is provided at a circumferential position of the tension roller 42, which applies tension to the intermediary image transfer member 40 in combination with the driving roller 41. Passing through the secondary image transfer unit 60, the intermediary image transfer member 40 turns toward the tension roller 42. The intermediary image transfer member cleaning blade 46 performs cleaning thereat. Then, the intermediary image transfer member 40 turns toward the primary image transfer units 50Y, 50M, 50C, and 50K.

Developer recovery replenishing devices 70Y, 70M, 70C, and 70K adjust the density (i.e., concentration) of liquid developers recovered from the image carriers 10Y, 10M, 10C, and 10K and the developing units 30Y, 30M, 30C, and 30K, and then re-supplies it to the developer containers 31Y, 31M, 31C, and 31K, respectively.

Figure 14:
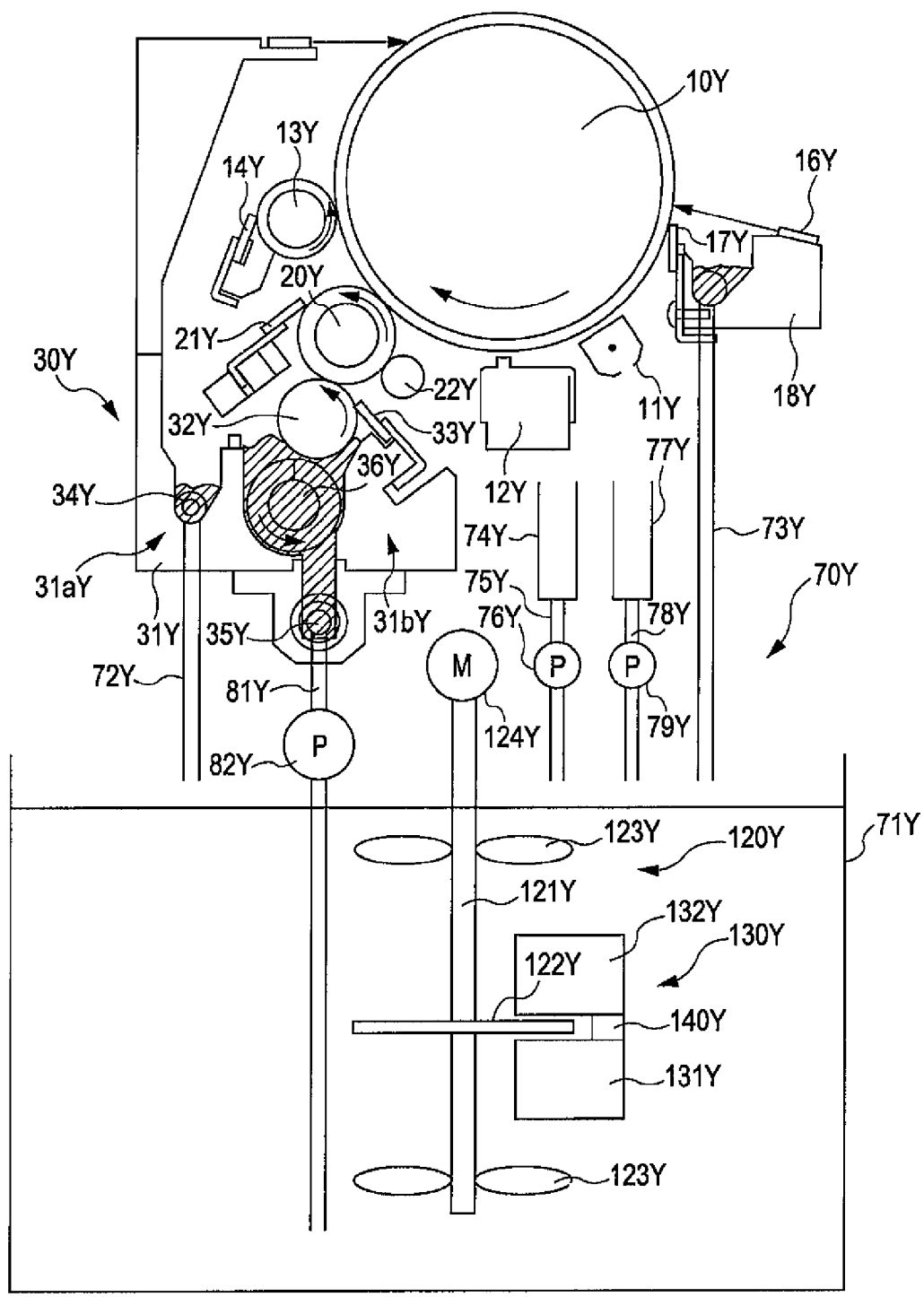
FIG. 14 is a sectional view that schematically illustrates an example of main components of an image formation unit and a developing unit according to an exemplary embodiment of the invention.

Next, the developer recovery replenishing devices 70Y, 70M, 70C, and 70K are explained below. FIG. 14 is a sectional view that schematically illustrates an example of the configuration of a developer recovery replenishing device according to an exemplary embodiment of the invention. Since the configuration of each of the developer recovery replenishing devices 70M, 70C, and 70K is the same as that of the developer recovery replenishing device 70Y, the developer recovery replenishing device 70Y for the yellow (Y) developer is explained.

As illustrated in FIG. 14, the developer recovery replenishing device 70Y is provided with the containing member 71Y for retaining a liquid developer whose concentration is to be adjusted. A concentrated developer and carrier liquid are respectively replenished from a developer tank 74Y and a carrier liquid tank 77Y to the containing member 71 for concentration adjustment.

In the present embodiment of the invention, a liquid developer is recovered (i.e., collected) from the developing unit 30Y and the image carrier 10Y. A developer recovery screw 34Y stirs a liquid developer recovered in a recovery-side reservoir 31aY of the developing unit 30Y. The stirred liquid developer flows through a developing-unit recovery channel 72Y and returns to the liquid developer containing member 71Y. On the other hand, a liquid developer is recovered from the image carrier 10Y by means of a cleaning device that is made up of an image carrier cleaning blade 17Y and a developer recovery unit 18Y. The collected liquid developer flows through an image-carrier recovery channel 73Y and returns to the liquid developer containing member 71Y.

A developer of high concentration is replenished from the developer tank 74Y to the liquid developer containing member 71Y through a developer replenishment channel 75Y and a developer pump 76Y. Carrier liquid is replenished from the carrier liquid tank 77Y to the liquid developer containing member 71Y through a carrier liquid replenishment channel 78Y and a carrier liquid pump 79Y. A structure that utilizes gravity to open and close valves, etc. for replenishment may be adopted as a substitute for the pumps.

The liquid developer retained in the liquid developer containing member 71Y is supplied to a supply-side reservoir 31bY of the developer container 31Y through a developer supply channel 81Y and a developer supply pump 82Y.

A concentration detection apparatus 120Y is provided with a rotating shaft 121, a transparent propeller 122Y, a stirring propeller 123Y, and a concentration detection unit 130Y. The transparent propeller 122Y is an example of a moving section according to an aspect of the invention. The stirring propeller 123Y is an example of various kinds of stirring members. Both the transparent propeller 122Y and the stirring propeller 123Y are provided on the rotating shaft 121. The common shaft 121 rotates when driven by a motor 124Y.

The concentration detection unit 130Y has the same structure as that of the concentration detection unit 130 illustrated in FIGS. 1 to 12. Therefore, an explanation thereof is omitted here.

Figure 15:
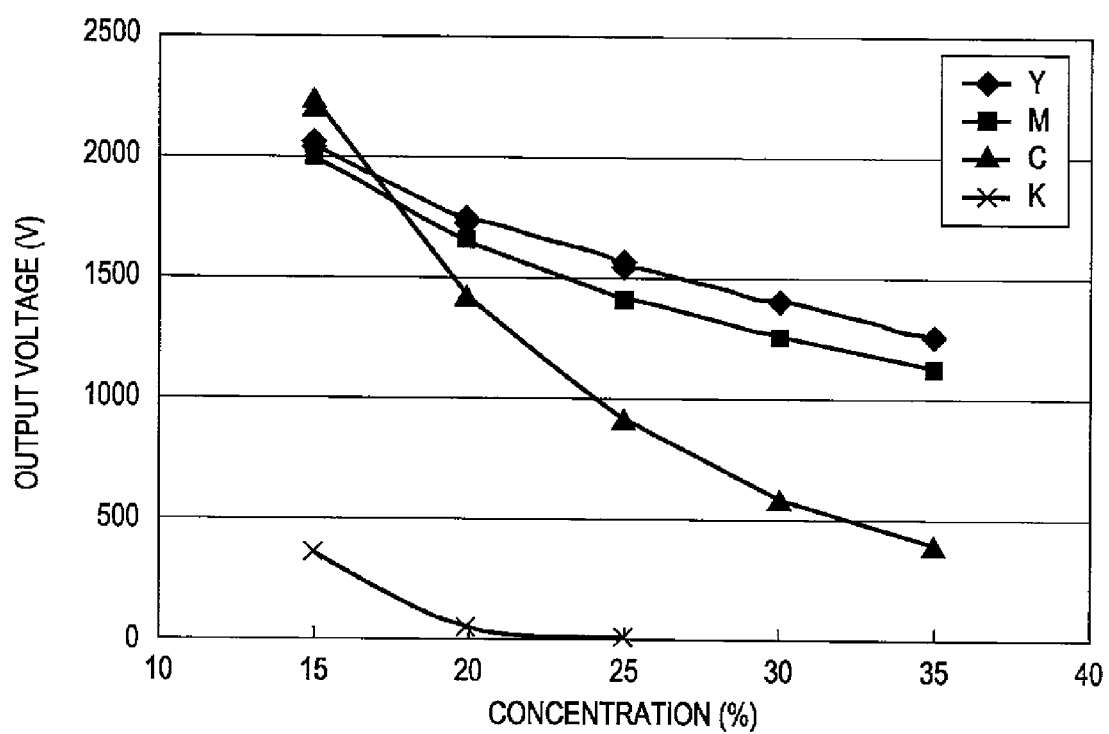
FIG. 15 is a graph that shows the relationship between the concentration of a liquid developer of each color and the output voltage of a concentration detection apparatus when the same value is set for clearances.

FIG. 15 is a graph that shows the relationship between the concentration of a liquid developer of each color and the output voltage of the concentration detection apparatus 120 when the same value is set for the clearances 133. As understood from the graph, the output voltage for black K as the first color differs substantially from those for the remaining colors, that is, cyan C as the second color, yellow Y as the third color, and magenta M as the fourth color for the same concentration. In addition, the output voltage for cyan C as the second color, the output voltage for yellow Y as the third color, and the output voltage for magenta M as the fourth color differ from one another for the same concentration. As described above, when the same distance is set for the clearance 133, the output voltage varies because of a difference in the transmission factors of the respective colors.

Figure 16:
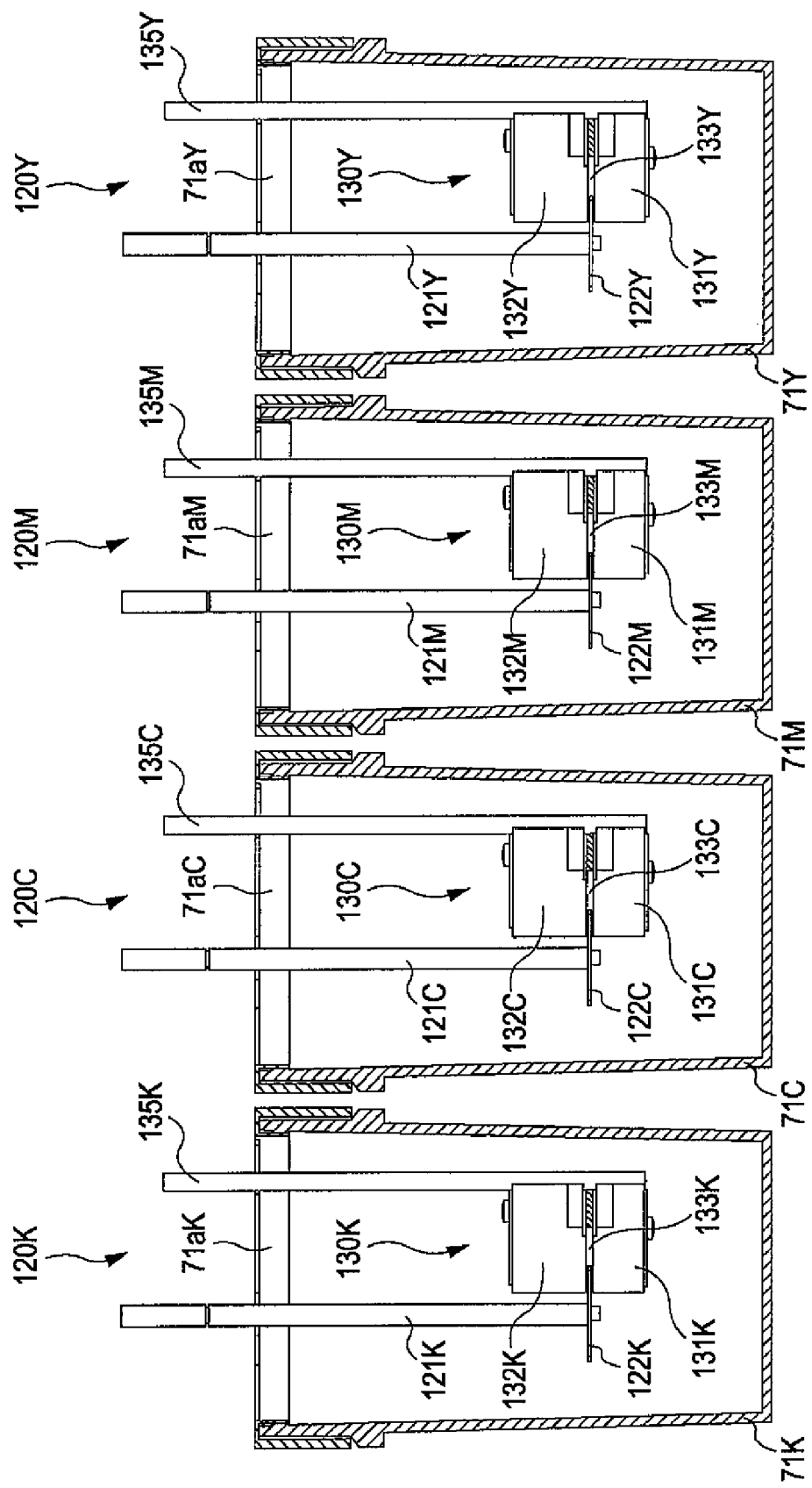
FIG. 16 is a diagram that schematically illustrates an example of a concentration detection apparatus that is applied to an image formation apparatus according to an exemplary embodiment of the invention.

FIG. 16 is a diagram that schematically illustrates an example of a concentration detection apparatus that is applied to an image formation apparatus according to an exemplary embodiment of the invention. As illustrated in FIG. 16, in the present embodiment of the invention, the clearance 133 is set at different distance values for plural liquid developer colors.

For example, a clearance 133K for black K is set at a distance value that is different from distance values of clearances 133C, 133Y, and 133M for cyan C, yellow Y, and magenta M. Specifically, it is preferable to set the clearance 133K for black K, which has a low transmission factor, at a value that is smaller than values of the clearances 133C, 133Y, and 133M for cyan C, yellow Y, and magenta M.

Or, the clearance 133K for black K, the clearance 133C for cyan C, and the clearance 133Y/M for yellow Y and magenta M may be set at distance values that are different from one another. Specifically, as a preferred example, the clearance 133 may be set as follows. The clearance 133K for black K, which has the lowest transmission factor, is set at a value that is smaller than a value of the clearance 133C for cyan C, which has the second lowest transmission factor. The clearance 133C for cyan C is set at a value that is smaller than a value of the clearance 133Y/M for yellow Y and magenta M.

As another example, the clearances 133K, 133C, 133Y, and 133M for the respective colors may be set at values different from one another. In this preferred example, the clearance 133K for black K, which has the lowest transmission factor, is set at a value that is smaller than a value of the clearance 133C for cyan C, which has the second lowest transmission factor. The clearance 133C for cyan C is set at a value that is smaller than a value of the clearance 133M for magenta M, which has the second highest transmission factor. The clearance 133M for magenta M is set at a value that is smaller than a value of the clearance 133Y for yellow Y, which has the highest transmission factor.

With the structure of the concentration detection apparatus 120 according to the present embodiment of the invention, it is possible to adjust a gap between the light-emitting element 131a and the light-receiving element 132a depending on the transmission factor of liquid whose concentration is to be measured, thereby improving precision in concentration detection.

In addition, the concentration detection apparatus 120 according to the present embodiment of the invention offers cost reduction with a simple structure.

Moreover, the concentration detection apparatus 120 according to the present embodiment of the invention prevents or reduces the stagnation of liquid in the clearance 133 between the light-emitting element 131a and the light-receiving element 132a, thereby improving precision in concentration detection.

With the structure of an image formation apparatus according to the present embodiment of the invention, it is possible to adjust a gap between the light-emitting element 131a and the light-receiving element 132a depending on the colors of liquid developers having transmission factors different from one another. Therefore, it is possible to improve precision in concentration detection and thus form an image in high quality.

The entire disclosure of Japanese Patent Application No: 2008-261832, filed Oct. 8, 2008 is expressly incorporated by reference herein.

What is claimed is:

1. A concentration detection apparatus comprising:
a light-emitting element that emits light;
a light-emitting-element holding section that holds the light-emitting element;
a light-receiving element that receives light emitted from the light-emitting element;
a light-receiving-element holding section that holds the light-receiving element and is provided opposite to the light-emitting-element holding section with a gap therebetween;
a moving section that can move through or at the gap between the light-emitting-element holding section and the light-receiving-element holding section; and
a gap adjusting section that adjusts a value of the gap as a distance between the light-emitting-element holding section and the light-receiving-element holding section,
wherein the gap adjusting section includes a spacer that is provided between the light-emitting-element holding section and the light-receiving-element holding section and further includes a joining section that joins the light-emitting-element holding section and the light-receiving-element holding section with the spacer being provided therebetween.

2. The concentration detection apparatus according to claim 1, wherein the spacer is an elastic member.

3. The concentration detection apparatus according to claim 1, wherein the moving section has flexibility.

4. An image formation apparatus comprising:
a first container that contains a first liquid developer;
a first image carrier on which is formed a latent image;
a first developing section that develops the latent image formed on the first image carrier by means of the first liquid developer;
a first concentration detecting section that is provided in the first container, the first concentration detecting section including
a first light-emitting element that emits light, a first light-emitting-element holding section that holds the first light-emitting element,
a first light-receiving element that receives light emitted from the first light-emitting element,
a first light-receiving-element holding section that holds the first light-receiving element and is provided opposite to the first light-emitting-element holding section with a first gap therebetween, and
a first moving section that moves through or at the first gap;
a second container that contains a second liquid developer;
a second image carrier on which is formed a latent image;
a second developing section that develops the latent image formed on the second image carrier by means of the second liquid developer;
a second concentration detecting section that is provided in the second container, the second concentration detecting section including
a second light-emitting element that emits light, a second light-emitting-element holding section that holds the second light-emitting element,
a second light-receiving element that receives light emitted from the second light-emitting element,
a second light-receiving-element holding section that holds the second light-receiving element and is provided opposite to the second light-emitting-element holding section with a second gap therebetween, and
a second moving section that moves through or at the second gap; and
a transfer member onto which an image formed on the first image carrier and an image formed on the second image carrier are transferred, wherein
the first concentration detecting section further includes a first gap adjusting section that adjusts the first gap; and the second concentration detecting section further includes a second gap adjusting section that adjusts the second gap, and
the first and second gap adjusting sections each include a spacer that is provided between the light-emitting-element holding sections and the light-receiving-element holding sections, and a joining section that joins the light-emitting-element holding sections and the light-receiving-element holding sections with the spacer being provided therebetween.

5. The image formation apparatus according to claim 4 further comprising:
a third container that contains a third liquid developer;
a third image carrier on which is formed a latent image;
a third developing section that develops the latent image formed on the third image carrier by means of the third liquid developer;
a third concentration detecting section that is provided in the third container, the third concentration detecting section including
a third light-emitting element that emits light,
a third light-emitting-element holding section that holds the third light-emitting element,
a third light-receiving element that receives light emitted from the third light-emitting element,
a third light-receiving-element holding section that holds the third light-receiving element and is provided opposite to the third light-emitting-element holding section with a third gap therebetween, and
a third moving section that moves through or at the third gap;
a fourth container that contains a fourth liquid developer;
a fourth image carrier on which is formed a latent image;
a fourth developing section that develops the latent image formed on the fourth image carrier by means of the fourth liquid developer; and
a fourth concentration detecting section that is provided in the fourth container, the fourth concentration detecting section including
a fourth light-emitting element that emits light,
a fourth light-emitting-element holding section that holds the fourth light-emitting element,
a fourth light-receiving element that receives light emitted from the fourth light-emitting element,
a fourth light-receiving-element holding section that holds the fourth light-receiving element and is provided opposite to the fourth light-emitting-element holding section with a fourth gap therebetween, and
a fourth moving section that moves through or at the fourth gap.

* * * * *